United States Patent
Szafert et al.

(10) Patent No.: US 9,365,595 B1
(45) Date of Patent: Jun. 14, 2016

(54) METHOD OF CONVERTING POLYHEDRAL OLIGOMERIC SILSESQUIOXANE (POSS) TYPE T8 INTO TYPE 10

(71) Applicant: UNIWERSYTET WROCLAWSKI, Wroclaw (PL)

(72) Inventors: Slawomir Szafert, Wroclaw (PL); Mateusz Przemyslaw Janeta, Wroclaw (PL); Lukasz John, Wroclaw (PL)

(73) Assignee: UNIWERSYTET WROCLAWSKI, Wroclaw (PL)

( * ) Notice: Subject to any disclaimer, the term of this patent is extended or adjusted under 35 U.S.C. 154(b) by 0 days.

(21) Appl. No.: 14/852,253

(22) Filed: Sep. 11, 2015

(51) Int. Cl.
*C07F 7/12* (2006.01)
*C07F 7/21* (2006.01)

(52) U.S. Cl.
CPC .... *C07F 7/21* (2013.01); *C07F 7/12* (2013.01)

(58) Field of Classification Search
CPC .......................................................... C07F 7/12
USPC .......................................................... 556/406
See application file for complete search history.

(56) References Cited

PUBLICATIONS

Y. Kawakami et al., Chem Lett. 2007, 36, 792.*

* cited by examiner

*Primary Examiner* — Elvis O Price
(74) *Attorney, Agent, or Firm* — Andrew W. Chu; Craft Chu PLLC

(57) ABSTRACT

The conversion method of $T_8$ type Polyhedral Oligomeric Silsesquioxanes (POSS) into $T_{10}$ type compounds, includes treating octasilsesquioxane of the general formula $(RSiO_{1.5})_8$ (wherein R is hydride, ethyl, vinyl, 3-chloropropyl, 3-hydroxypropyl, phenyl, octyl, 3-decanaminepropyl, 3-benzamideamidepropyl group and 3-aminepropyl hydrochloride group) with at least 10-fold excess of organic acid giving decasilsesquioxane $(RSiO_{1.5})_{10}$. The reaction is conducted in air.

4 Claims, 3 Drawing Sheets

(a) random structure (b) ladder structure (c) open cage structure

R= hydrogen atom, alkyl group, aryl group, halogen or alkenyl group.

R= (1) -CH₂CH₂CH₂NH₃Cl;

(2) –H;

(3) -CH₂CH₃;

(4) –CH=CH₂;

(5) –CH₂CH₂CH₂Cl;

(6) –CH₂CH₂CH₂OH;

(7) –C₆H₅;

(8) -CH₂(CH₂)₆CH₃;

(9) -CH₂(CH₂)₂CNHC(O)CH₂(CH₂)₈CH₃;

(10) -CH₂(CH₂)₂CNHC(O)C₆H₅;

METHOD OF CONVERTING POLYHEDRAL OLIGOMERIC SILSESQUIOXANE (POSS) TYPE T8 INTO TYPE 10

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The subject of the invention is the conversion method of $T_8$ type Polyhedral Oligomeric Silsesquioxanes (POSS) to $T_{10}$ type compounds using acidic catalyst.

2. Description of Related Art Including Information Disclosed Under 37 CFR 1.97 and 37 CFR 1.98.

Most Polyhedral (multiwalled) Oligomeric Silsesquioxanes (POSS) are specific example of silsesquioxanes (SQ) which are described by the specific formula $(RSiO_{1.5})_n$, wherein R symbol indicate hydrogen atom, alkyl group, aryl group, halogen, alkenyl group and derivatives thereof, usually n have a value: 6, 8, 10, 12. SQ is most frequently prepared by hydrolysis and subsequent condensation of trifunctional silanes in slightly elevated or room temperature in and using basic and acidic catalyst. As a precursor for SQ synthesis specific silanes $RSiX_3$ (X=Cl, OR, OAc, $NH_2$ and other) are used which are easy to hydrolyse giving silanol groups and are further subjected to polycondensation. Hydrolysis speed depends on the type of substituent on silica atom which are not hydrolysed (bigger substituent, lower speed) and type of X function group. Besides, temperature, monomer concentration, amount of water added, type of solvent and catalyst are also influencing the efficiency. Polycondensation performed in such manner gives various structures of silsesquioxanes as presented on FIG. 1.

Apart from SQ presented above, POSS in small amounts are also generated during hydrolytic polycondensation reaction. Cage-formed and constructed from complete multiple one-and-half silicate $RSiO_{1.5}$ units SQ are also included. POSS are signed with $T_n$ symbol, wherein usually n have a 6, 8, 10, 12 value and indicate amount of silica atoms present in the corner of polyhedron.

Polyhedral oligomeric silsesquioxanes are prepared in general from organic trichloro- or trialkoxysilanes in hydrolytic polycondensation process described above. Most commonly used catalyst of this reaction are non-organic acid such as e.g. HCl, $H_2SO_4$ or bases (organic amines, metal hydroxides). It is necessary to use moderate amounts of water (most preferably in molar $H_2O/RSiX_3$ ratio=1:1) in order to maintain heterofunctional condensation instead of competitive homocondensation of silanols.

Typical POSS structures are presented on FIG. 2.

Most commonly found are type $T_8$ compounds due to presence of four interconnected $Si_4O_4$ with high rings stability which compose core of the cage. Generation of less thermodynamically unstable POSS such as $T_{10}$ or $T_{12}$ is a result of spontaneous conversion of $T_8$ type POSS. In general, they are produced with low efficiency as a by-products in reaction of POSS arms modification. Such $T_8$ cage modification into the bigger one was published by several research groups [(a) Y. Kawakami, K. Yamaguchi, T. Yokozawa, T. Serizawa, M. Hasegawa, Y. Kabe, Chem. Lett. 2007, 36, 792; (b) A. R. Bassindale, Z. Liu, I. A. Mackinnon, P. G. Taylor, Y. Yang, M. E. 100 Light, P. N. Horton, M. B. Hursthouse, Dalton Trans. 2003, 2945. (c) V. Ervithayasuporn, X. Wang, Y. Kawakami, Chem. Commun. 2009, 5130].

Nevertheless, these compounds most commonly were not isolated in a pure form. It is directly connected to the similarity in solubility for compounds of $T_8$, $T_{10}$, $T_{12}$ type and higher. Separation of POSS is particularly difficult when compounds, e.g. $T_{10}$ and $T_{12}$, exhibit similar physico-chemical properties.

Kawakami et al. described generation of POSS $T_8$, $T_{10}$ and $T_{12}$ during hydrolysis of 4-substituted phenyltriethoxysilan in presence of TBAF (tetrabutylammonium fluoride). Separation of POSS with different cage size is conducted by crystallization using different type of solvent solutions e.g. acetonitrile/THF (v/v, 1:1), pure hexane or ethanol/hexane mixtures (v/v, 1:4). Known ways to obtain $T_{10}$ and $T_{12}$ cages are presented in Table 1 based on publication: Lickiss, P. D.; Rataboul, F. Fully Condensed Polyhedral Oligosilsesquioxanes (POSS): From Synthesis to Application. Adv. Organomet. Chem. 2008, 57, 1-116.

TABLE 1

Examples of reaction conditions to obtain different $T_8$ or $T_{12}$ type silsesquioxanes.

| Cage size | Type of R substituent | Starting compound and reaction conditions | Efficiency [%] | The value of the chemical shift $^{29}$Si NMR |
|---|---|---|---|---|
| $T_{10}$ | —H | $HSiCl_3$ + c-$C_6H_{12}$/PhMe + $H_2SO_4$ | 3.6 | −86.25 |
| | —Cp | $CpSiCl_3$ + $H_2O$, THF + $(NH_4)_2CO_3$, 7 days | 67 | −71.50 |
| | —CH=$CH_2$ | $[CH_2$=$CHSi(OEt)_2]_2O$ + $H_2O$, TBF, THF/$CH_2Cl_2$, 2 days | 26 | −81.48 |
| | —$C_6H_5$ | $PhSiCl_3$ + $H_2O$, toluene, KOH, 9 h, subsequently recrystallization from benzene/n-hexane mixture | — | — |
| $T_{12}$ | —H | $HSiCl_3$ + $H_2O$, $H_2SO_4$, cyclohexane/toluene, 6 h | 3.5 | −85.78, −87.76 |
| | —CH=$CH_2$ | $[CH_2$=$CHSi(OEt)_2]_2O$ + $H_2O$, TBF, THF/$CH_2Cl_2$, 2 days | 15 | −81.34, −83.35 |
| | —$C_6H_5$ | $PhSiCl_3$ + $H_2O$, KOH, THF, reflux, 3 days | — | — |

Besides above methods there is a method know in the literature for obtaining $T_{10}$ type cages by conversion of SQ using fluoride ions. Rikowski et al. found that $T_{10}$ and $T_{12}$ POSSs are generated as a result of $T_8$ cage conversion using NaF and 18-crown-6 as a catalyst. This conversion has given following efficiencies: 28% $T_8$, 61% $T_{10}$ and 11% $T_{12}$.

Surprisingly, it has been discovered that usage of organic acid in form of triflic acid as a catalyst in conversion process of polyhedral oligomeric silsesquioxane constructed as a closed cage consisting of eight $RSiO_{1.5}$ units ($T_8$ cage; $[RSiO_{1.5}]_8$) into the cage made of ten $RSiO_{1.5}$ units ($T_{10}$ cage; $[RSiO_{1.5}]_8$) enabled obtaining high efficiency of the process and isolation of crude reaction products in pure form.

SUMMARY OF THE INVENTION

The essence of the invention is the conversion method of $T_8$ type Polyhedral Oligomeric Silsesquioxanes (POSS) into $T_{10}$ type compounds, characterised in that octasilsesquioxane of the general formula $(RSiO_{1.5})_8$ (wherein R is hydride, ethyl, vinyl, 3-chloropropyl, 3-hydroxypropyl, phenyl, octyl, 3-decanaminepropyl, 3-benzamideamidepropyl group and 3-aminepropyl hydrochloride group) was treated with at least 10-fold excess of organic acid giving decasilsesquioxane $(RSiO_{1.5})_{10}$, wherein reaction is conducted in air.

Preferably, an organic acid is trifluoromethanesulfonic acid ($CF_3SO_3H$).

Preferably, $T_8$ type POSS is initially dissolved in polar solvent, preferably dimethylsulfoxide (DMSO), methanol, acetone, N,N-dimethylformamide (DMF), acetonitrile, hexamethylphosphoramide (HMPA), N-methylformamide.

Preferably, type $T_8$ POSS conversion reaction into $T_{10}$ type POSS is conducted for at least 2 h in temperature of 40° C.

Reaction was conducted in DMSO solution in temperature of 40° C. End product was isolated through extraction from solid postreaction mixture using acetone.

Identification of compounds was performed using elemental analysis, infra-red spectroscopy, NMR spectroscopy ($^1H$, $^{13}O$ and $^{29}Si$) and mass spectrometry.

BRIEF DESCRIPTION OF THE DRAWINGS

The invention was described in more details in exemplary embodiments and in the figures.

DETAILED DESCRIPTION OF THE DRAWINGS

Example 1

Figures 1, 2:
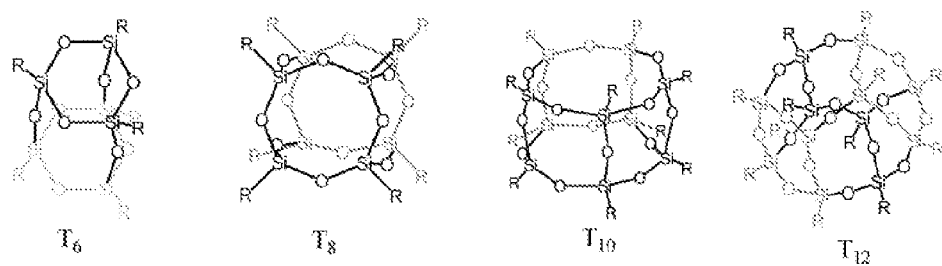
FIG. 1 shows a schematic view of exemplary SQ structures.
FIG. 2 shows a schematic view exemplary POSS structures.
Figure 3:
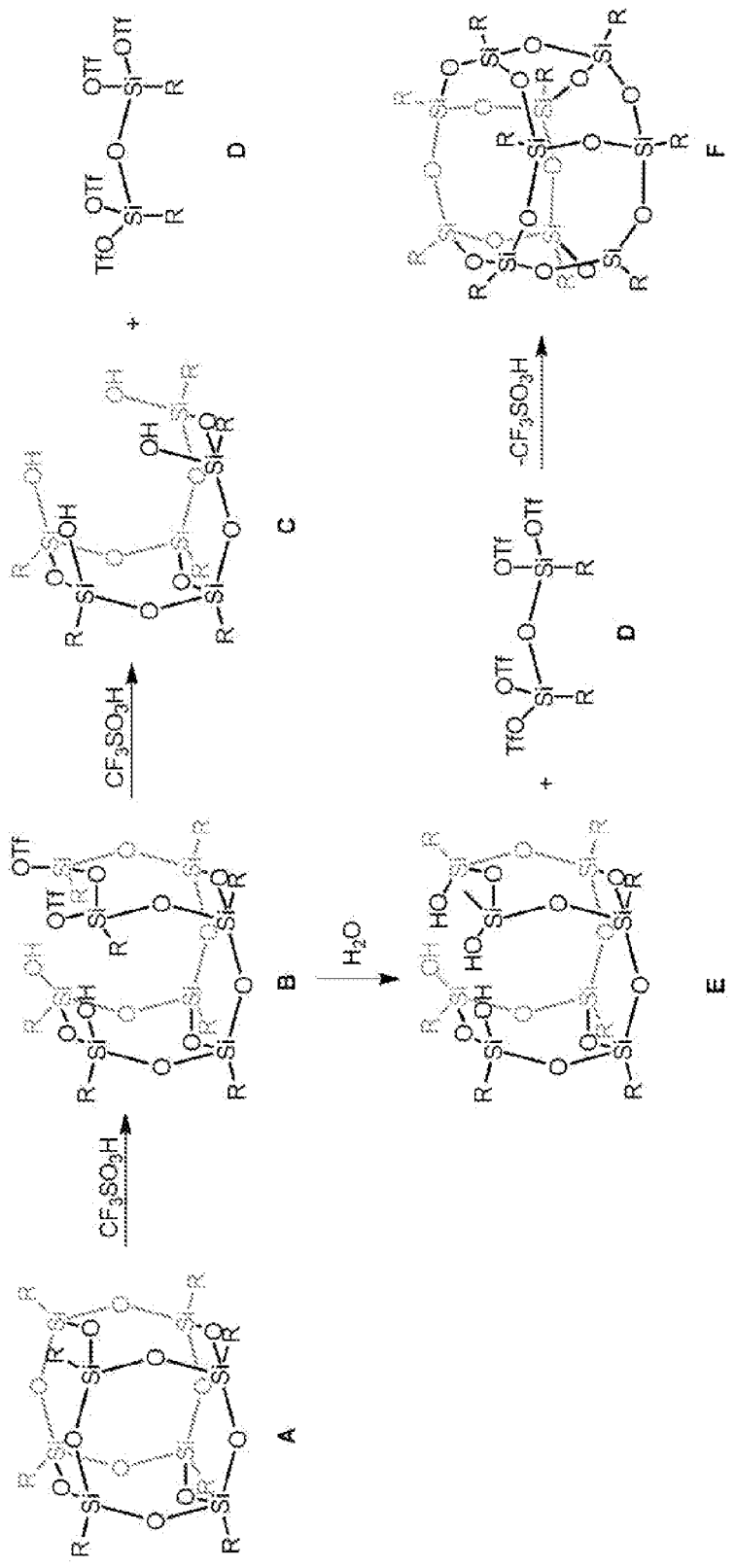
FIG. 3 shows a schematic view of a mechanism of conducted reaction.
Figure 4:
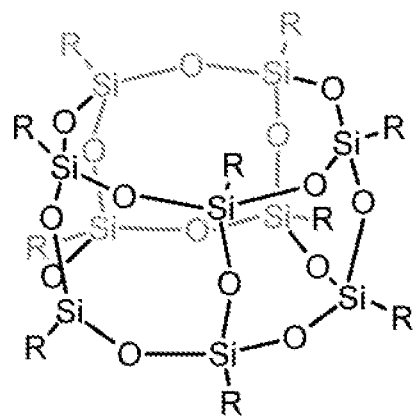
FIG. 4 shows a schematic view of illustrations of obtained $T_{10}$ type compounds.

Triflic acid (12 eq, 1.022 mmol, 0.154 g, 0.0905 mL) was added dropwise to the solution of oct(3-aminepropyl)silsesquioxane hydrochloride (0.100 g, 0.0852 mmol) in DMSO (5 mL). Obtained solution was mixed for 2 hours in temperature of 40° C. under oxygen and was subsequently chilled to room temperature, solvent was purged with nitrogen stream. Obtained yellow sediment was rinsed with acetone (3×15 mL). Filtered and solvent was subsequently evaporated obtaining white powder which is deca(3-aminepropyl)silsesquioxane triflic salt with 44% efficiency (0.078 g).

Elemental analysis calculated (%) for $C_{40}H_{88}F_{30}N_{10}O_{45}S_{10}Si_{10}$ (2600.62): C, 18.48; H, 3.41; N, 5.39; S, 12.31. found: C, 18.55; H, 3.31; N, 5.32; S, 12.42.

FT-IR (cm$^{-1}$, KBr pellets): $\nu_{N-H}$=3041 (s), $\delta_{NH3}$=1615 (m), $\nu_{C-N}$=1507 (m), $\nu_{C-F}$=1267 (s), $\nu_{Si-C}$=1226 (m), $\nu_{Si-O-Si}$=1138 (s), $\nu_{SO3}$=1031 (s), $\nu_{S-N}$=640 (s).

$^1H$ NMR (500 MHz, DMSO-d$_6$, 300 K): δ=7.52 (s, 30H, $NH_3^+$), 2.73 (t, $^3J_{HH}$=7.2 Hz, 20H, $CH_2NH_3^+$), 1.49 (m, 20H, $SiCH_2CH_2CH_2NH_3^+$), 0.59 (t, $^3J_{HH}$=8.6 Hz, 20H, $SiCH_2$)

$^{13}C\{^1H\}$ NMR (126 MHz, DMSO-d$_6$, 300 K): δ=122.5 (q, $^1J_{C-F}$=317 Hz, $CF_3SO_3^-$), 41.1 (s, $SiCH_2CH_2CH_2NH_3^+$), 20.6 (s, $SiCH_2CH_2CH_2NH_3^+$), 8.2 (s, $SiCH_2CH_2CH_2NH_3^+$).

HR-MS (ESI+, TOF, MeOH), m/z: 567.7398 [M+3H-6CF$_3$SO$_3$H]$^{3+}$ (theoret. 567.7367), 517.7479 [M+3H-7CF$_3$SO$_3$H]$_{3+}$ (theoret. 517.7504), 467.7697 [M+3H-8CF$_3$SO$_3$H]$^{3+}$ (theoret. 467.7638), 426.1133 [M+4H-6CF$_3$SO$_3$H]$_{4+}$ (theoret. 426.0545), 417.7837 [M+3H-9CF$_3$SO$_3$H]$^{3+}$ (theoret. 417.7771), 401.4678 [M+5H-4CF$_3$SO$_3$H]$^{5+}$ (theoret. 401.2029), 388.5721 [M+5H-7CF$_3$SO$_3$H]$^{5+}$ (theoret. 388.5646), 371.7947 [M+5H-5CF$_3$SO$_3$H]$^{5+}$ (theoret. 371.0371), 367.8035 [M+4H-10CF$_3$SO$_3$H]$^{5+}$ (theoret. 367.7905), 351.0974 [M+4H-8CF$_3$SO$_3$H]$^{4+}$ (theoret. 351.0746), 313.5899 [M+4H-9CF$_3$SO$_3$H]$^{4+}$ (theoret. 313.5847), 311.0972 [M+5H-7CF$_3$SO$_3$H]$^{5+}$ (theoret. 311.0531), 281.0678 [M+5H-8CF$_3$SO$_3$H]$^{5+}$ (theoret. 281.0612), 276.0995 [M+4H-10CF$_3$SO$_3$H]$^{4+}$ (theoret. 276.0947), 250.8448 [M+5H-9CF$_3$SO$_3$H]$^{5+}$ (theoret. 250.8676).

$^{29}Si\{^1H\}$ NMR (59.6 MHz, DMSO-d6, 20° C.): δ=−68.48 (s, $T^3$).

Example 2

Deca(hydrydo)silsesquioxane was obtained in analogy to example 1 using octa(hydrydo)silsesquioxane as a starting compound (0.036 g, 0.0852 mmol), reaction was conducted in acetone (5 mL). White powder was obtained with 40% efficiency (0.018 g).

Elemental analysis calculated (%) for $H_{10}O_{15}Si_{10}$ (530.97): C, 0.00; H, 1.90; N, 0.00. found: C, 0.00; H, 1.92; N, 0.00.

HR-MS (ESI+, TOF, MeOH), m/z: 530.7781 [M+H]$^+$ (theoret. 530.7785).

Example 3

Deca(ethyl)silsesquioxane was obtained in analogy to example 1 using octa(ethyl)silsesquioxane as a starting compound (0.055 g, 0.0852 mmol), reaction was conducted in DMF (5 mL). White powder was obtained with 39% efficiency (0.043 g).

Elemental analysis calculated (%) for $C_{20}H_{50}O_{15}Si_{10}$ (811.50) C, 29.60; H, 6.21; N, 0.00. found: C, 29.66; H, 6.28; N, 0.00.

HR-MS (ESI+, TOF, CHCl$_3$), m/z: 811.0922 [M+H]$^+$ (theoret. 811.0915).

Example 4

Deca(vinyl)silsesquioxane was obtained in analogy to example 1 using octa(vinyl)silsesquioxane as a starting compound (0.054 g, 0.0852 mmol), reaction was conducted in N-methylformamide (10 mL). White powder was obtained with 45% efficiency (0.030 g).

Elemental analysis calculated (%) for $C_{20}H_{30}O_{15}Si_{10}$ (791.35) C, 30.36; H, 3.82; N, 0.00. found: C, 30.31; H, 3.85; N, 0.00.

HR-MS (ESI+, TOF, THF), m/z: 790.9348 [M+H]$^+$ (theoret. 790.9350).

Example 5

Deca(3-chloropropyl)silsesquioxane was obtained in analogy to example 1 using octa(3-chloropropyl)silsesquioxane as a starting compound (0.088 g, 0.0852 mmol), reaction was conducted in methanol (10 mL). White powder was obtained with 48% efficiency (0.053 g).

Elemental analysis calculated (%) for $C_{30}H_{60}Cl_{10}O_{15}Si_{10}$ (1296.27) C, 27.80; H, 4.67; N, 0.00; Cl, 27.35. found: C, 27.84; H, 4.63; N, 0.00; Cl, 27.31.

HR-MS (ESI+, TOF, THF), m/z: 1290.8578 [M+H]$^+$ (theoret. 1290.8583).

Example 6

Deca(3-hydroxypropyl)silsesquioxane was obtained in analogy to example 1 using octa(3-hydroxypropyl)silsesquioxane as a starting compound (0.113 g, 0.0852 mmol), reaction was conducted in DMSO (5 mL). White powder was obtained with 53% efficiency (0.050 g).

Elemental analysis calculated (%) for $C_{30}H_{70}O_{25}Si_{10}$ (1111.77) C, 32.41; H, 6.35; N, 0.00. found: C, 32.48; H, 6.28; N, 0.00.

HR-MS (ESI+, TOF, CHCl$_3$), m/z: 1111.1968 $[M+H]^+$ (theoret. 1111.1972).

Example 7

Deca(phenyl)silsesquioxane was obtained in analogy to example 1 using octa(phenyl)silsesquioxane as a starting compound (0.088 g, 0.0852 mmol), reaction was conducted in HPMA (10 mL). White powder was obtained with 44% efficiency (0.048 g).

Elemental analysis calculated (%) for $C_{60}H_{50}O_{15}Si_{10}$ (1291.94) C, 55.78; H, 3.90; N, 0.00. found: C, 55.75; H, 3.95; N, 0.00.

HR-MS (ESI+, TOF, CHCl$_3$), m/z: 1291.0908 $[M+H]^+$ (theoret. 1291.0915).

Example 8

Deca(octyl)silsesquioxane was obtained in analogy to example 1 using octa(ethyl)silsesquioxane as a starting compound (0.113 g, 0.0852 mmol), reaction was conducted in DMF (5 mL). White powder was obtained with 51% efficiency (0.072 g).

Elemental analysis calculated (%) for $C_{80}H_{170}O_{15}Si_{10}$ (1653.12) C, 58.13; H, 10.37; N, 0.00. found: C, 58.10; H, 10.31; N, 0.00.

HR-MS (ESI+, TOF, CHCl$_3$), m/z: 1652.0305 $[M+H]^+$ (theoret. 1652.0305).

Example 9

Deca(3-decanamidepropyl)silsesquioxane was obtained in analogy to example 1 using octa(3-decanamidepropyl)silsesquioxane as a starting compound (0.180 g, 0.0852 mmol), reaction was conducted in acetonitrile (5 mL). White powder was obtained with 43% efficiency (0.097 g).

Elemental analysis calculated (%) for $C_{130}H_{260}N_{10}O_{25}Si_{10}$ (2644.45) C, 59.05; H, 9.91; N, 5.30. found: C, 59.01; H, 9.93; N, 5.29.

FT-IR (cm$^{-1}$, KBr pellets): $v_{N-H}$=3278 (s), $v_{C-H}$=2931 (m), $v_{C-H}$=2871 (m), $v_{C=O}$=1636 (5), $\delta_{NH}$=1558 (s), 1457 (w), $v_{C-N}$=1383 (m), (w), 1272 (w), $V_{ring-asym.\ Si-O-Si}$=1122 (5), $\delta_{O-Si-O}$=698 (w), $\delta_{O-Si-O}$=472 (w).

HR-MS (ESI+, TOF, CHCl$_3$), m/z: 1321.8756 $[M+2H]^{2+}$ (theoret. 1321.8610), 881.5648 $[M+3H]^{3+}$ (theoret. 881.5764).

$^1$H NMR (500 MHz, CDCl$_3$, 300 K): δ=3.15 (t, $^3J_{HH}$=7.0 Hz, 20H, CH$_2$NH), 2.51 (t, $^3J_{HH}$=7.4 Hz, 20H, C(O)CH$_2$), 1.52 (br, 40H, SiCH$_2$CH$_2$CH$_2$ and C(O)CH$_2$ CH$_2$, 1.20-1.25 (br, 120H, —CH$_2$—), 0.82 (t, $^3J_{HH}$=7.0 Hz, 30H, CH$_3$), 0.56 (t, $^3J_{HH}$=8.4 Hz, 20H, SiCH$_2$).

$^{13}$C{$^1$H} NMR (126 MHz, CDCl$_3$, 300 K): δ=169.3 (s, C=O), 42.2 (s, SiCH$_2$CH$_2$CH$_2$NH), 31.9 (s, C(O)CH$_2$), 30.7, 29.5, 29.4, 29.3, 29.3, 29.2, (5, —CH$_2$—), 22.9 (s, SiCH$_2$CH$_2$CH$_2$NH), 22.7 (s, C(O)CH$_2$CH$_2$), 14.1 (s, CH$_3$), 9.2 (s, SiCH$_2$CH$_2$CH$_2$NH).

$^{29}$Si{$^1$H} NMR (59.6 MHz, 59.6 MHz, CDCl$_3$, 300 K): δ=−68.54 (5, T$^3$).

Example 10

Deca(3-benzamideamidepropyl)silsesquioxane was obtained in analogy to example 1 using octa(3-benzamideamidepropyl)silsesquioxane as a starting compound (0.146 g, 0.0852 mmol), reaction was conducted in DMF (5 mL). White powder was obtained with 60% efficiency (0.110 g).

Elemental analysis calculated (%) for $C_{100}H_{120}N_{10}O_{25}Si_{10}$ (1653.12) C, 56.05; H, 5.64; N, 6.54. found: C, 56.01; H, 5.68; N, 6.57.

HR-MS (ESI+, TOF, CHCl$_3$), m/z: 2141.6187 $[M+H]^+$ (theoret. 2141.6192).

POSS application possibilities are vast and depend on substituents attached to the POSS cage corners. Variety of POSS derivatives are known with substituents such as hydrogen atoms or such a groups as: alkoxide, amine, acryl, metacryl, halogen, nitrile, phenyl, fluoralkyl, alkenyl, thiol and other.

POSS compounds gives higher mechanical and thermal durability to the materials which they modify. Potential and real applications include e.g. resistors to obtain new materials for lithography, high-temperature greases, materials with low dielectric constant, pigment dispersants. POSS compounds can be used in biomaterial chemistry as a systems for drug delivery, antimicrobial coatings, component of dental nanocomposites. POSS can be used in electronics and optoelectronics (in LED diodes), in separation membranes for oil/water systems and in materials for space industry. POSS are also used in cosmetics, printing inks and to modify material surface in order to obtain hydrophobic, self-cleaning properties and higher wear resistance.

We claim:

1. A method of converting $T_8$ type Polyhedral Oligomeric Silsesquioxanes (POSS) into $T_{10}$ type compounds, comprising the steps of:
    treating octasilsesquioxane of general formula $(RSiO_{1.5})_8$ (wherein R is hydride, ethyl, vinyl, 3-chloropropyl, 3-hydroxypropyl, phenyl, octyl, 3-decanaminepropyl, 3-benzamideamidepropyl group and 3-aminepropyl hydrochloride group) with at least 10-fold excess of organic acid giving decasilsesquioxane $(RSiO_{1.5})_{10}$; and conducting the reaction in air.

2. Method according to claim 1, wherein said organic acid is comprised of trifluoromethanesulfonic acid ($CF_3SO_3H$).

3. Method according to claim 1, said method further comprising: dissolving said octasilsesquioxane in polar solvent, wherein said polar solvent is selected from one of a group consisting of dimethylsulfoxide (DMSO), methanol, acetone, N,N-dimethylformamide (DMF), acetonitrile, hexamethylfosforamide (HMPA), and N-methylformamide.

4. Method according to claim 1, wherein the step of conducting said reaction is at least two hour at a temperature of 40° C.

* * * * *